(12) United States Patent
Buisson et al.

(10) Patent No.: US 11,123,480 B2
(45) Date of Patent: Sep. 21, 2021

(54) PURGE DEVICE FOR A SYSTEM FOR ADMINISTERING MEDICAL TREATMENT FLUIDS

(71) Applicant: DORAN INTERNATIONAL, Toussieu (FR)

(72) Inventors: Philippe Buisson, Toussieu (FR); Brice Fiore, Bischheim (FR)

(73) Assignee: DORAN INTERNATIONAL, Toussieu (FR)

( * ) Notice: Subject to any disclaimer, the term of this patent is extended or adjusted under 35 U.S.C. 154(b) by 228 days.

(21) Appl. No.: 16/336,378

(22) PCT Filed: Sep. 19, 2017

(86) PCT No.: PCT/FR2017/052498
§ 371 (c)(1),
(2) Date: Mar. 25, 2019

(87) PCT Pub. No.: WO2018/055274
PCT Pub. Date: Mar. 29, 2018

(65) Prior Publication Data
US 2019/0209771 A1    Jul. 11, 2019

(30) Foreign Application Priority Data
Sep. 26, 2016 (FR) ..................... 16/59014

(51) Int. Cl.
*A61M 5/14* (2006.01)
*A61M 39/10* (2006.01)
(Continued)

(52) U.S. Cl.
CPC ........ *A61M 5/1408* (2013.01); *A61M 39/105* (2013.01); *A61M 39/223* (2013.01);
(Continued)

(58) Field of Classification Search
CPC .............. A61M 39/105; A61M 39/223; A61M 39/225; A61M 39/1055;
(Continued)

(56) References Cited

U.S. PATENT DOCUMENTS 4,804,369 A    2/1989 Lapeyre et al.
9,814,866 B1 *    11/2017 Goswami .............. A61M 27/00
(Continued)

FOREIGN PATENT DOCUMENTS

EP    2217305 A2    8/2010
FR    2581315 A1    11/1986
(Continued)

OTHER PUBLICATIONS

International Search Report for Application No. PCT/FR2017/052498.
Written Opinion for Application No. PCT/FR2017/052498.

*Primary Examiner* — Emily L Schmidt
*Assistant Examiner* — Leah J Swanson
(74) *Attorney, Agent, or Firm* — Cantor Colburn LLP

(57) ABSTRACT

This purge device comprises a connection element comprising a plurality of fluid flow channels which each comprise a proximal end, intended to be connected fluidically to a respective fluid flow conduit of a flow tube, and a distal end opposite the respective proximal end, and a plurality of fluid flow openings which are each connected fluidically to a respective fluid flow channel; a closure element comprising a fluid evacuation opening and a closure part, the closure element being mounted movably with respect to the connection element and being configured to occupy a plurality of closure positions, in each of which the closure part closes the distal end of a fluid flow channel and the fluid evacuation opening is connected fluidically to the fluid flow opening associated with the fluid flow channel, of which the distal (Continued)

end is closed by the closure part; and a connection nozzle intended to be connected to a catheter.

19 Claims, 2 Drawing Sheets

(51) Int. Cl.
*A61M 39/22* (2006.01)
*A61M 39/24* (2006.01)

(52) U.S. Cl.
CPC ... *A61M 39/225* (2013.01); *A61M 2005/1403* (2013.01); *A61M 2039/226* (2013.01); *A61M 2039/2486* (2013.01)

(58) Field of Classification Search
CPC .... A61M 2039/0202; A61M 2039/082; A61M 2039/224; A61M 2039/226; A61M 2039/229; A61M 5/1407–1409; A61M 2005/1402; A61M 2005/1403; A61M 2005/1401; A61M 5/16827; A61M 5/16877; A61M 5/16881; A61M 2039/0205; A61M 2039/2486
See application file for complete search history.

(56) References Cited

U.S. PATENT DOCUMENTS

2003/0181850 A1  9/2003  Diamond et al.
2006/0047249 A1  3/2006  Shubayev et al.

FOREIGN PATENT DOCUMENTS

WO    2007033319 A1    3/2007
WO    2016037648 A1    3/2016

* cited by examiner

PURGE DEVICE FOR A SYSTEM FOR ADMINISTERING MEDICAL TREATMENT FLUIDS

CROSS REFERENCE TO RELATED APPLICATIONS

This application is a National Stage of PCT Application No. PCT/FR2017/052498 filed on Sep. 19, 2017, which claims priority to French Patent Application No. 16/59014 filed on Sep. 26, 2016, the contents each of which are incorporated herein by reference thereto.

TECHNICAL FIELD

The present invention concerns a purge device for a medical treatment fluids administration system.

BACKGROUND

The document EP2217305 discloses a medical treatment fluids administration system, comprising in particular:
- a casing provided with several connection elements on each of which a container can be connected, and further comprising several liquid passage conduits, each liquid passage conduit including a proximal end portion fluidly connected to a respective connection element and a distal end portion opposite to the respective proximal end portion,
- a flow tube containing several fluid flow conduits which are substantially parallel and extend over the entire length of the flow tube, the flow tube including a distal end portion intended to be connected to a catheter and a proximal end portion coupled to the casing so that each fluid flow conduit of the flow tube is fluidly connected to a fluid passage conduit.

Such a configuration of the administration system described in the document EP2217305 allows simultaneously administering various medical treatment liquids to a patient without prior mixing of these liquids within the casing and the fluid flow tube, and therefore limiting the drug reactions and the precipitation formation within the administration system therefore accurately controlling the administration of each fluid. These arrangements more particularly allow accurately controlling the administered quantity and the administration flow rate of each liquid.

The drawback of such an administration system however lies in the fact that in order to purge an administration route formed by a fluid passage conduit and the respective fluid flow conduit (for example when a drug solution is desired to be replaced with another), it is necessary to provide a valve between the flow tube and the catheter. However, the use of such valve to purge an administration route of the aforementioned administration system implies either stopping the other administration routes of the administration system, or also purging the other administration routes and therefore losing the drug solutions that are in these other administration routes. Furthermore, the presence of such a valve is likely to induce a risk of mixing different drug solutions during their passage through the valve.

BRIEF SUMMARY

The present invention aims at overcoming these drawbacks.

The technical problem at the origin of the invention consists therefore in providing a purge device which has a simple structure and which is economical, while allowing the purge of a fluid flow conduit of the flow tube without stopping the treatment of the patient and without any risk of loss of drug solutions contained in the other fluid flow conduits of the flow tube.

To this end, the present invention concerns a purge device for a medical treatment fluids administration system, comprising:
- a coupling element intended to be coupled to a distal end portion of a flow tube including a plurality of fluid flow conduits, the coupling element comprising:
  - a plurality of fluid flow channels, each fluid flow channel comprising a proximal end intended to be fluidly connected to a respective fluid flow conduit of the flow tube and a distal end opposite to the respective proximal end, and
  - a plurality of fluid flow apertures, each fluid flow aperture being fluidly connected to a respective fluid flow channel,
- a closure element comprising a fluid evacuation aperture and a closure portion, the closure element being movably mounted relative to the coupling element and being configured to occupy a plurality of closed positions; in each of which the closure portion closes off the distal end of a fluid flow channel and the fluid evacuation aperture is fluidly connected to the fluid flow aperture which is fluidly connected to the fluid flow channel whose distal end is closed off by the closure portion, and to occupy at least one released position in which the closure portion releases the distal ends of the fluid flow channels and the fluid evacuation aperture is fluidly isolated from the fluid flow apertures, and
- a connection end fitting intended to be connected to a catheter, the connection end fitting comprising an outlet orifice configured to be fluidly connected to the distal ends of the fluid flow channels and intended to be fluidly connected to the catheter.

Such a configuration of the coupling element and of the closure element allows easily purging a fluid flow conduit of a flow tube, and this simply by moving the closure element into a closed position in which the closure portion closes off the distal end of the fluid flow channel connected to the fluid flow conduit to be purged. In such a closed position, the fluid to be purged flows through the fluid flow aperture associated with the fluid flow channel closed off by the closure portion and the fluid evacuation aperture.

Furthermore, since in each closed position the closure portion is configured to close off the distal end of only one fluid flow channel, the purge of a fluid flow conduit using the purge device according to the present invention has no impact on the other fluid flow conduits.

Consequently, the purge device according to the present invention allows purging a fluid flow conduit of a flow tube without stopping the treatment of the patient, and without any risk of loss of drug solutions contained in the other fluid flow conduits of the flow tube.

The purge device may further have one or more of the following characteristics, taken alone or in combination.

According to one embodiment of the invention, in each closed position occupied by the closure element, the fluid evacuation aperture is arranged facing a respective fluid flow aperture.

According to one embodiment of the invention, the outlet orifice of the connection end fitting is fluidly connected to the distal ends of all the fluid flow channels when the closure element is in the at least one released position, and is fluidly connected to the distal ends of the fluid flow channels that are not closed off by the closure portion when the closure element is in any one of the closed positions.

According to one embodiment of the invention, the closure element is mounted movable in rotation relative to the coupling element.

According to one embodiment of the invention, the closure element includes a hollow body extending along a longitudinal axis and provided with an axial through passage extending over the entire length of the hollow body, the coupling element extending at least partly in the axial through passage, the fluid evacuation aperture being provided on the hollow body and opening into the axial through passage.

According to one embodiment of the invention, the closure element is mounted movable in rotation about an axis of rotation which is substantially coincident with the longitudinal axis of the closure element. In other words, the closure element is mounted movable in rotation about its longitudinal axis.

According to one embodiment of the invention, the hollow body has a generally tubular shape.

According to one embodiment of the invention, the axial through passage is generally cylindrical.

According to one embodiment of the invention, the fluid evacuation aperture radially opens into the axial through passage.

According to one embodiment of the invention, the coupling element comprises a mounting portion extending at least partly in the axial through passage of the hollow body, the mounting portion of the coupling element being provided with fluid flow apertures.

According to one embodiment of the invention, the closure portion is a closure finger.

According to one embodiment of the invention, the closure portion extends from a distal end of the hollow body.

According to one embodiment of the invention, the closure portion extends radially towards the inside of the hollow body.

According to one embodiment of the invention, each fluid flow aperture opens into an outer peripheral surface of the coupling element.

According to one embodiment of the invention, the outer peripheral surface of the coupling element is generally cylindrical.

According to one embodiment of the invention, the mounting portion of the coupling element is externally delimited by the outer peripheral surface into which each fluid flow aperture opens.

According to one embodiment of the invention, each fluid flow aperture extends radially.

According to one embodiment of the invention, the fluid flow apertures are angularly offset from each other relative to a longitudinal axis of the coupling element. According to one embodiment of the invention, the fluid flow apertures extend in a same extension plane.

According to one embodiment of the invention, the fluid flow apertures are regularly angularly offset from each other relative to the longitudinal axis of the coupling element.

According to one embodiment of the invention, the fluid flow channels extend substantially parallel.

According to one embodiment of the invention, the connection end fitting comprises a discharge conduit intended to be connected to a recovery container, the discharge conduit being fluidly connected to the fluid evacuation aperture provided on the closure element. It should be noted that the recovery container can be any type of container, and for example a flexible bag.

According to one embodiment of the invention, the discharge conduit is equipped with a check-valve configured to enable a flowing of the fluid only from the fluid evacuation aperture to the recovery container.

According to one embodiment of the invention, the connection end fitting comprises a mounting portion in which the closure element is at least partly mounted.

According to one embodiment of the invention, the hollow body is at least partly mounted in the mounting portion of the connection end fitting.

According to one embodiment of the invention, the mounting portion of the connection end fitting is generally cylindrical.

According to one embodiment of the invention, the discharge conduit extends from an outer peripheral surface of the mounting portion, and for example radially outwardly from the outer peripheral surface of the mounting portion.

According to one embodiment of the invention, the mounting portion of the connection end fitting includes an inner surface provided with an annular groove, the discharge conduit and the fluid evacuation aperture opening into the annular groove.

According to one embodiment of the invention, the connection end fitting at least in partly delimits an inner chamber into which the distal ends of the fluid flow channels open, the outlet orifice of the connection end fitting opening into the inner chamber. The inner chamber may for example be at least partly delimited by the coupling element and the connection end fitting.

According to one embodiment of the invention, the connection end fitting comprises a frustoconical connecting portion intended to be connected to the catheter, the frustoconical connecting portion being fluidly connected to the outlet orifice.

According to one embodiment of the invention, the connection end fitting is of the Luer or Luer Lock type.

According to one embodiment of the invention, the connection end fitting comprises an internally threaded connecting portion intended to be connected to the catheter, the internally threaded connecting portion surrounding the frustoconical connecting portion.

According to one embodiment of the invention, the coupling element comprises a distal end surface, for example substantially flat distal end surface, into which the distal ends of the fluid flow channels open. Advantageously, the distal end surface at least partly delimits the inner chamber.

According to one embodiment of the invention, the coupling element comprises a coupling portion configured to receive, for example by force fitting, the distal end portion of the flow tube.

According to one embodiment of the invention, the closure element includes a bearing portion configured to cooperate with the mounting portion of the connection end fitting so as to limit the depth of insertion of the closure element into the mounting portion. The bearing portion may comprise a bearing surface, for example an annular bearing surface, configured to cooperate with a proximal end of the mounting portion of the connection end fitting.

According to one embodiment of the invention, the closure element includes an abutment portion configured to cooperate with the coupling element so as to limit the depth of insertion of the coupling element into the closure element, and more particularly to limit the depth of insertion of the coupling element into the axial through passage of the hollow body. The abutment portion may comprise an abutment surface, for example an annular abutment surface, configured to cooperate with the coupling element, and for example with the coupling portion of the coupling element.

According to one embodiment of the invention, the coupling element includes an annular notch in which a proximal end portion of the hollow body is received. The annular notch may, for example, be provided on the coupling portion of the coupling element, and axially open in the direction of the closure element.

According to one embodiment of the invention, the coupling element comprises a plurality of coupling pins, each coupling pin being hollow and being intended to be engaged in a distal end portion of a respective fluid flow conduit of the flow tube. Advantageously, the coupling portion comprises the coupling pins.

According to one embodiment of the invention, the proximal end of each fluid flow channel opens into the free end of a respective coupling pin.

According to one embodiment of the invention, the coupling element comprises a central fluid flow conduit, and the fluid flow channels are distributed, for example regularly distributed, around the central fluid flow conduit.

According to one embodiment of the invention, the coupling element and the connection end fitting are mounted stationary relative to one another.

According to one embodiment of the invention, at least one of the coupling element, the closure element and the connection end fitting is made of plastic material, and for example transparent plastic material.

According to one embodiment of the invention, the closure element is configured to occupy a plurality of released positions in each of which the closure portion releases the distal ends of the fluid flow channels and the fluid evacuation aperture is fluidly isolated from the fluid flow apertures.

According to one embodiment of the invention, the purge device could comprise detection means configured to detect the passage of the closure member into a closed position, and for example from a released position to a closed position, and warning means configured to emit a warning signal, for example audible or visual warning signal, when the closure member is maintained in a closed position for a period of time greater than a predetermined threshold value. The warning signal can also be transmitted to an operator, for example by Wifi or Bluetooth. These arrangements allow to avoid maintaining by error or omission the closure element in a closed position, and therefore to ensure secure administration of the various fluids.

According to one embodiment of the invention, the purge device could comprise a plurality of coupling elements and a plurality of closure elements, each closure element being associated with a respective coupling element, and each coupling element being intended to be coupled to a distal end portion of a respective flow tube.

BRIEF DESCRIPTION OF THE DRAWINGS

In any case, the invention will be better understood using the following description with reference to the appended schematic drawings showing, by way of a non-limiting example, an embodiment of this purge device.

DETAILED DESCRIPTION

Figure 1:
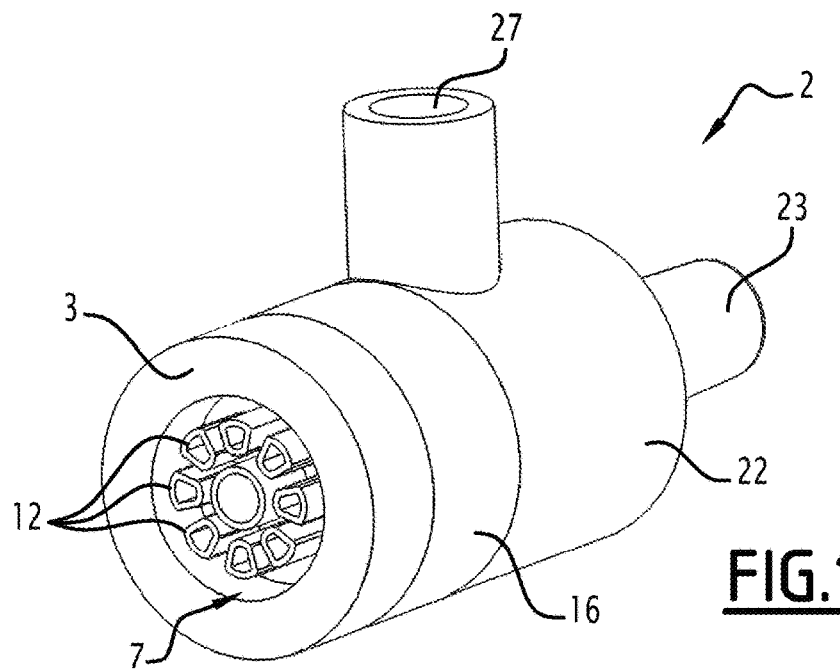
FIG. 1 is a perspective view of a purge device according to the invention.

FIGS. 1 to 6 show a purge device 2 for a medical treatment fluid administration system, and for example for an administration system as described in the document EP2217305.

As shown in FIGS. 2 to 5, the purge device 2 comprises a coupling element 3 intended to be coupled to a distal end portion of a flow tube 4 belonging to a medical treatment fluid administration system and including a plurality of fluid flow conduits 5. The coupling element 3 may for example be made of plastic material.

The coupling element 3 more particularly comprises a coupling portion 6 including a receiving housing 7 configured to receive, by force fitting, the distal end portion of the flow tube 4. According to the embodiment shown in the figures, the receiving housing 7 is generally cylindrical and opens into a proximal end face 3.1 of the coupling element 3. The coupling portion 6 further comprises a plurality of coupling pins 8 extending in the receiving housing 7 and substantially parallel relative to each other. Each coupling pin 8 is hollow and is intended to be engaged in a distal end portion of a respective fluid flow conduit 5 of the flow tube 4.

The coupling element 3 further comprises a mounting portion 9 externally delimited by an outer peripheral surface 11 which is generally cylindrical and which extends substantially coaxially with the receiving housing 7.

The coupling element 3 in addition comprises a plurality of fluid flow channels 12 extending over substantially the entire length of the coupling element 3. Each fluid flow channel 12 comprises a proximal end 12.1 opening into a free end of a respective coupling pin 8 and therefore intended to be fluidly connected to a respective fluid flow conduit 5 of the flow tube 4, and a distal end 12.2 opposite to the respective proximal end 12.1 and opening into a distal end surface 13, for example substantially flat distal end surface, of the mounting portion 9. Advantageously, the fluid flow channels 12 extend substantially parallel.

According to the embodiment shown in the figures, the coupling element 3 also comprises a central fluid flow conduit 14 around which the fluid flow channels 12 are regularly distributed. Advantageously, the central fluid flow conduit 14 comprises a proximal end 14.1 opening into the free end of a respective coupling pin 8 and therefore intended to be fluidly connected to a respective fluid flow conduit 5 of the flow tube 4, and a distal end 14.2 opposite to the respective proximal end 14.1 and opening into the distal end surface 13 of the mounting portion 8.

Figure 2:
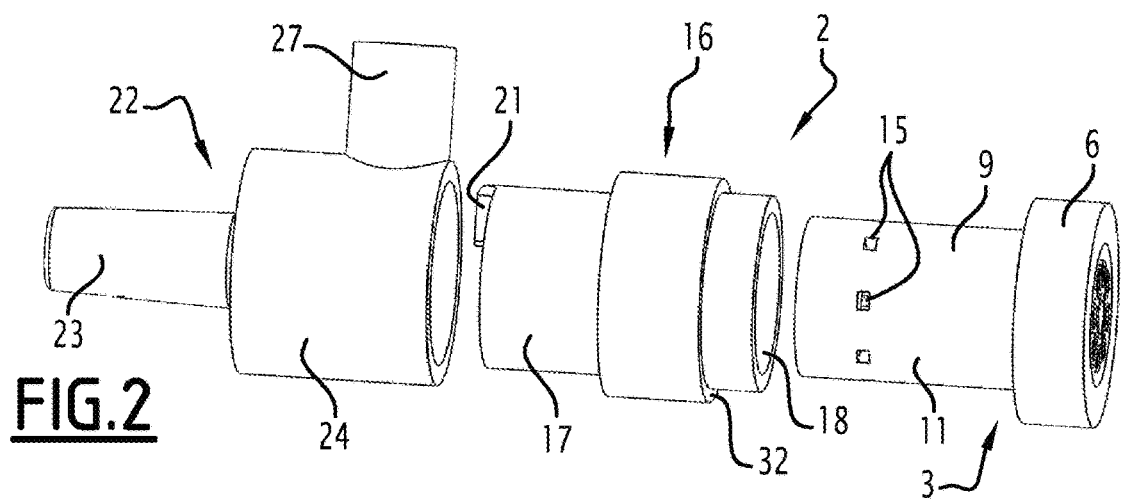
FIG. 2 is an exploded perspective view of the purge device of FIG. 1.

As shown in particular in FIG. 2, the coupling element 3 comprises a plurality of fluid flow apertures 15 formed on the mounting portion 9. Each fluid flow aperture 15 is fluidly connected to a respective fluid flow channel 12, and opens into the outer peripheral surface 11 of the mounting portion 8. According to the embodiment shown in the figures, the fluid flow apertures 15 extend radially in a same extension plane, and are regularly angularly offset from each other relative to a longitudinal axis of the coupling element 3.

Figure 5:
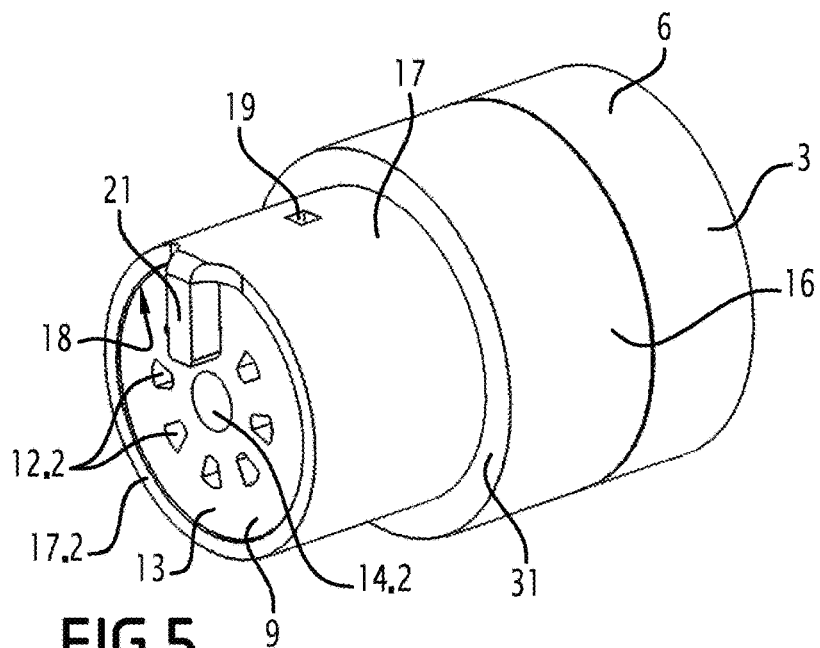
FIG. 5 is a perspective view of the coupling element of FIG. 4 inserted into a closure member of the purge device of FIG. 1.

As more particularly shown in FIGS. 2 and 5, the purge device 2 further comprises a closure element 16 which may for example be made of plastic material. The closure element 16 includes a hollow body 17 having a generally tubular shape and extending along a longitudinal axis. The hollow body 17 is provided with an axial through passage 18 which is generally cylindrical and extending over the entire length of the hollow body 17. The axial through passage 18 thus has a substantially constant cross section over its entire length.

Figure 3:
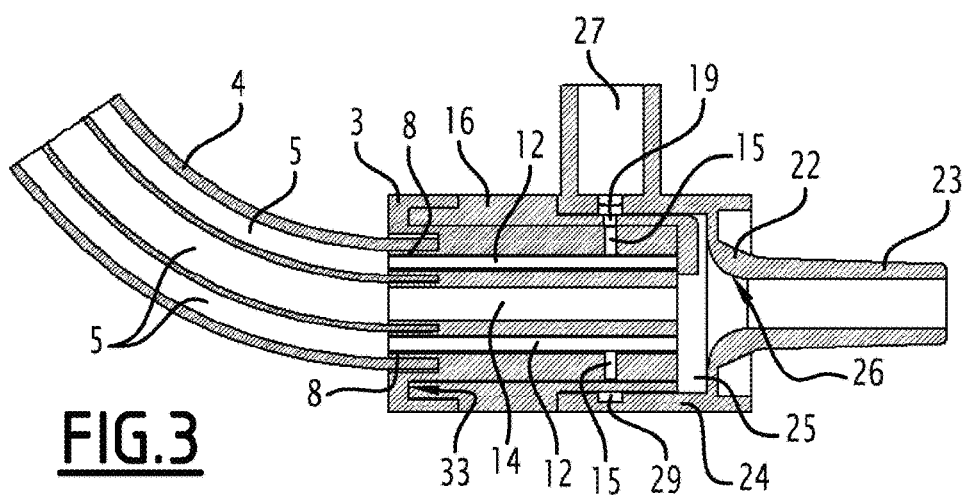
FIG. 3 is a longitudinal sectional view of the purge device of FIG. 1.
Figure 4:
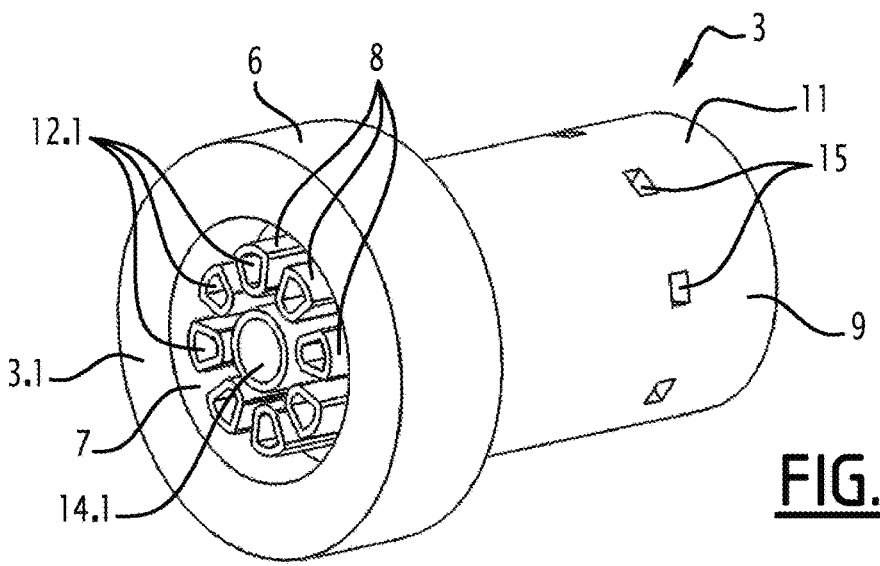
FIG. 4 is a perspective view of a coupling element of the purge device of FIG. 1.

As is more particularly seen from FIGS. 3 and 5, the mounting portion 9 of the coupling element 3 extends in the axial through passage 18, and the outer peripheral surface 11 of the mounting portion 9 has a diameter substantially corresponding to the inner diameter of the axial through passage 18. As a result, the closure element 16 is mounted movable in rotation relative to the coupling element 3 about an axis of rotation coincident with the longitudinal axes respectively of the closure element 16 and the coupling element 3.

The closure element 16 further comprises a fluid evacuation aperture 19 provided on the hollow body 17 and opening into the axial through passage 18, and a closure portion 21, for example having the shape of a closure finger, extending radially inwardly from a distal end 17.2 of the hollow body 17.

The closure element 16 is more particularly configured to occupy a plurality of closed positions angularly offset from each other and in each of which the closure portion 21 closes off the distal end 12.2 of a respective fluid flow channel 12 and the fluid evacuation aperture 19 is located facing the fluid flow aperture 15 which is fluidly connected to the fluid flow channel 12, whose distal end 12.2 is closed off by the closure portion 21. Thus, in each closed position, the fluid evacuation aperture 19 is fluidly connected to the fluid flow aperture 15 associated with the fluid flow channel 12, whose distal end 12.2 is closed off by the closure portion 21.

The closure element 16 is further configured to occupy a plurality of released positions angularly offset from each other and in each of which the closure portion 21 releases the distal ends 12.2 of the fluid flow channels 12 and the fluid evacuation aperture 19 is fluidly isolated from the fluid flow apertures 15.

Figure 6:
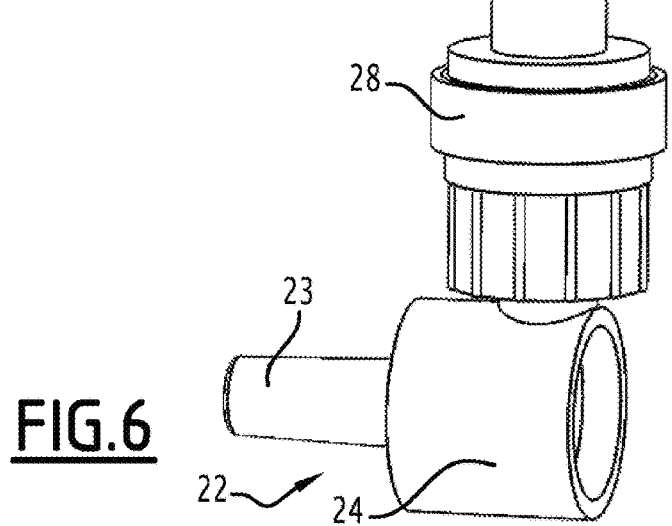
FIG. 6 is a perspective view of a connection end fitting of the purge device of FIG. 1.

As more particularly shown in FIGS. 2 and 6, the purge device 2 further comprises a connection end fitting 22 which is mounted stationary relative to the coupling element 3 and intended to be connected to a catheter, and which can for example be of the Luer or Luer Lock type. According to the embodiment shown in the figures, the connection end fitting 22 is of the Luer type and includes a frustoconical connecting portion 23 intended to be connected to the catheter. The connection end fitting 22 could, however, be of the Luer Lock type and thus further comprise a connecting portion which is internally threaded and surrounding the frustoconical connecting portion 23.

The connection end fitting 22 further comprises a mounting portion 24 which is tubular and generally cylindrical, and in which the hollow body 17 is partially mounted. Advantageously, the inner diameter of the mounting portion 24 substantially corresponds to the outer diameter of the hollow body 17. According to the embodiment shown in the figures, the mounting portion 24 of the connection end fitting 22 and the mounting portion 9 of the coupling element 3 delimit an inner chamber 25 into which the distal ends 12.2 of the fluid flow channels 12 open and in which the closure portion 21 extends.

The connection end fitting 22 in addition comprises an outlet orifice 26 opening into the inner chamber 25 and fluidly connected to the frustoconical connecting portion 23.

The connection end fitting 22 also comprises a discharge conduit 27 intended to be connected to a recovery container (not shown in the figures), such as a flexible bag or any other type of container. The discharge conduit 27 is fluidly connected to the fluid evacuation aperture 19 provided on the closure element 16, and is equipped with a check-valve 28 configured to enable a flowing of a fluid only from the fluid evacuation aperture 19 to the recovery container. According to the embodiment shown in the figures, the discharge conduit 27 extends radially outwardly from the outer peripheral surface of the mounting portion 24, and the inner surface of the mounting portion 24 is provided with an annular groove 29 extending around the hollow body 17 and into which the discharge conduit 27 and the fluid evacuation aperture 19 open.

As more particularly shown in FIGS. 3 and 5, the closure element includes an annular bearing surface 31 configured to cooperate with a proximal end of the mounting portion 24 of the connection end fitting 22 so as to limit the depth of insertion of the hollow body 17 into the mounting portion 24, and an annular abutment surface 32 configured to cooperate with the coupling portion 6 of the coupling element 3 so as to limit the depth of insertion of the mounting portion 9 of the coupling element 3 into the axial through passage 18 of the hollow body 17.

Furthermore, according to the embodiment shown in the figures, the coupling element 3 includes an annular notch 33 in which a proximal end portion of the hollow body 17 is received. The annular notch 33 may, for example, be provided on the coupling portion 6 of the coupling element 3, and axially open in the direction of the closure element 16.

A method for purging a fluid flow conduit of a flow tube 4 belonging to a medical treatment fluid administration system using the purge device 2 of the present invention will now be described.

Such a purge method comprises the following steps:

coupling the coupling portion 6 of the coupling element 3 to a distal end portion of the flow tube 4, connecting the frustoconical connecting portion 23 of the connection end fitting 22 to a catheter, positioning the closure element 16 in a closed position in which the closure portion 21 closes off the distal end 12.2 of the fluid flow channel 12, whose proximal end 12.1 is fluidly connected to the fluid flow conduit 5 to be purged, purging the fluid flow conduit 5 to be purged via the fluid flow aperture 15 which is fluidly connected to the fluid flow channel 12, whose distal end 12.2 is closed off by the closure portion 21, the fluid evacuation aperture 19 and the discharge conduit 27, recovering the purged fluid out of the flow conduit 5 of the fluid to be purged in a recovery container connected to the discharge conduit 27, a backflow of fluid to the coupling element 3 being prevented by the check-valve 28.

It should be noted that the step of positioning of the closure element 16 can be easily performed for example by providing on the one hand a reading mark on the closure element 16 and on the other hand a plurality of positioning marks on the coupling element 3, each positioning mark corresponding to a predetermined closed position of the closure element 16, that is to say to the closure of the distal end 12.2 of a predetermined fluid flow channel 12.

According to one embodiment of the invention, the purge device could comprise detection means configured to detect the passage of the closure member from a released position to a closed position, and to emit a warning signal, for example audible or visual warning signal, when the closure member is maintained in a closed position for a period of time greater than a predetermined threshold value.

It goes without saying that the invention is not limited to the sole embodiment of this purge device, described above as example, it encompasses on the contrary all the variants.

The invention claimed is:

1. A purge device for a medical treatment fluids administration system, comprising:
   a coupling element intended to be coupled to a distal end portion of a flow tube including a plurality of fluid flow conduits, the coupling element comprising:
   a plurality of fluid flow channels, each fluid flow channel comprising a proximal end intended to be fluidly connected to a respective fluid flow conduit of the flow tube and a distal end opposite to the respective proximal end, and
   a plurality of fluid flow apertures, each fluid flow aperture emerging in a respective fluid flow channel between the proximal and distal ends thereof,
   a closure element comprising a fluid evacuation aperture and a closure portion, the closure element being movably mounted relative to the coupling element and being configured to occupy a plurality of closed positions in each of which the closure portion closes off the distal end of one fluid flow channel of the plurality of fluid flow channels and the fluid evacuation aperture is fluidly connected to the fluid flow aperture which emerges in the fluid flow channel whose distal end is closed off by the closure portion, and to occupy at least one released position in which the closure portion releases the distal ends of the plurality of fluid flow channels and the fluid evacuation aperture is fluidly isolated from the fluid flow apertures, and
   a connection end fitting intended to be connected to a catheter, the connection end fitting comprising an outlet orifice configured to be fluidly connected to the distal ends of the plurality of fluid flow channels and intended to be fluidly connected to the catheter.

2. The purge device according to claim 1, wherein the closure element is mounted movable in rotation relative to the coupling element.

3. The purge device according to claim 2, wherein the closure element includes a hollow body extending along a longitudinal axis and provided with an axial through passage extending over an entire length of the hollow body, the coupling element extending at least partly in the axial through passage, the fluid evacuation aperture being provided on the hollow body and opening into the axial through passage.

4. The purge device according to claim 3, wherein the closure portion extends from a distal end of the hollow body.

5. The purge device according to claim 4, wherein the closure portion extends radially towards the inside of the hollow body.

6. The purge device according to claim 5, wherein each fluid flow aperture opens into an outer peripheral surface of the coupling element.

7. The purge device according to claim 6, wherein the fluid flow apertures are angularly offset from each other relative to a longitudinal axis of the coupling element.

8. The purge device according to claim 7, wherein the connection end fitting comprises a discharge conduit intended to be connected to a recovery container, the discharge conduit being fluidly connected to the fluid evacuation aperture provided on the closure element.

9. The purge device according to claim 1, wherein the closure element includes a hollow body extending along a longitudinal axis and provided with an axial through passage extending over an entire length of the hollow body, the coupling element extending at least partly in the axial through passage, the fluid evacuation aperture being provided on the hollow body and opening into the axial through passage.

10. The purge device according to claim 9, wherein the closure portion extends from a distal end of the hollow body.

11. The purge device according to claim 9, wherein the closure portion extends radially towards the inside of the hollow body.

12. The purge device according to claim 1, wherein each fluid flow aperture opens into an outer peripheral surface of the coupling element.

13. The purge device according to claim 1, wherein the fluid flow apertures are angularly offset from each other relative to a longitudinal axis of the coupling element.

14. The purge device according to claim 1, wherein the connection end fitting comprises a discharge conduit intended to be connected to a recovery container, the discharge conduit being fluidly connected to the fluid evacuation aperture provided on the closure element.

15. The purge device according to claim 14, wherein the discharge conduit is equipped with a check-valve configured to enable a flowing of a fluid only from the fluid evacuation aperture to the recovery container.

16. The purge device according to claim 1, wherein the connection end fitting comprises a mounting portion in which the closure element is at least partly mounted.

17. The purge device according to claim 1, wherein the connection end fitting at least in partly delimits an inner chamber into which the distal ends of the plurality of fluid flow channels open, the outlet orifice of the connection end fitting opening into the inner chamber.

18. The purge device according to claim 1, wherein the connection end fitting comprises a frustoconical connecting portion intended to be connected to the catheter, the frustoconical connecting portion being fluidly connected to the outlet orifice.

19. The purge device according to claim 1, wherein the coupling element comprises a plurality of coupling pins, each coupling pin being hollow and being intended to be engaged in a distal end portion of a respective fluid flow conduit of the flow tube.

* * * * *